(12) United States Patent
Wilde

(10) Patent No.: US 7,932,229 B2
(45) Date of Patent: Apr. 26, 2011

(54) COMPOSITIONS AND METHODS FOR THE CONTROL OF MAMMARY CELL NUMBER

(75) Inventor: Colin James Wilde, Ayr (GB)

(73) Assignee: AvantiCell Science Ltd, Auchincruive (GB)

( * ) Notice: Subject to any disclaimer, the term of this patent is extended or adjusted under 35 U.S.C. 154(b) by 765 days.

(21) Appl. No.: 11/666,143

(22) PCT Filed: Oct. 21, 2005

(86) PCT No.: PCT/GB2005/004068
§ 371 (c)(1),
(2), (4) Date: Jun. 20, 2007

(87) PCT Pub. No.: WO2006/043079
PCT Pub. Date: Apr. 27, 2006

(65) Prior Publication Data
US 2008/0221040 A1 Sep. 11, 2008

(30) Foreign Application Priority Data
Oct. 21, 2004 (GB) .................................. 0423352.4

(51) Int. Cl.
*A61K 38/00* (2006.01)
*A61K 38/04* (2006.01)
*A61K 31/00* (2006.01)
*A61K 39/395* (2006.01)
*C12P 21/08* (2006.01)
*C07K 16/00* (2006.01)
*G01N 31/00* (2006.01)
*G01N 33/574* (2006.01)

(52) U.S. Cl. .... 514/19.4; 530/328; 530/327; 530/387.7; 514/1.1; 436/6; 424/138.1; 435/7.23

(58) Field of Classification Search ........................ None
See application file for complete search history.

(56) References Cited

U.S. PATENT DOCUMENTS
2004/0097714 A1   5/2004   Maubois et al. ............. 530/399
2006/0178311 A1*  8/2006   Wilde et al. .................... 514/15

FOREIGN PATENT DOCUMENTS
EP     1 568 377     8/2005
WO    WO 01/64234    9/2001
WO    WO 03/006500   1/2003
WO    WO 03/018606   3/2003
WO    WO 2004/113378 12/2004

OTHER PUBLICATIONS

Lahov, et al. "Antibacterial and Immunostimulating Casein-Derived Substances From Milk: Casecidin, Isracidin Peptides", *Food and Chemical Toxicology, XX, XX*, vol. 34, No. 1, 1996, pp. 131-145.

* cited by examiner

*Primary Examiner* — Maury Audet
(74) *Attorney, Agent, or Firm* — Drinker Biddle & Reath LLP

(57) ABSTRACT

The present invention provides new methods and uses of peptides in effecting a reduction in mammary cell number. The discovery that these peptides reduce mammary cell number further enables the use of these peptides in the treatment of cancer where the peptides can be used to reduce cell number and accordingly reduce or prevent tumour development. The inventor has further shown that the peptides have specific utility in the treatment of breast cancer.

4 Claims, 9 Drawing Sheets

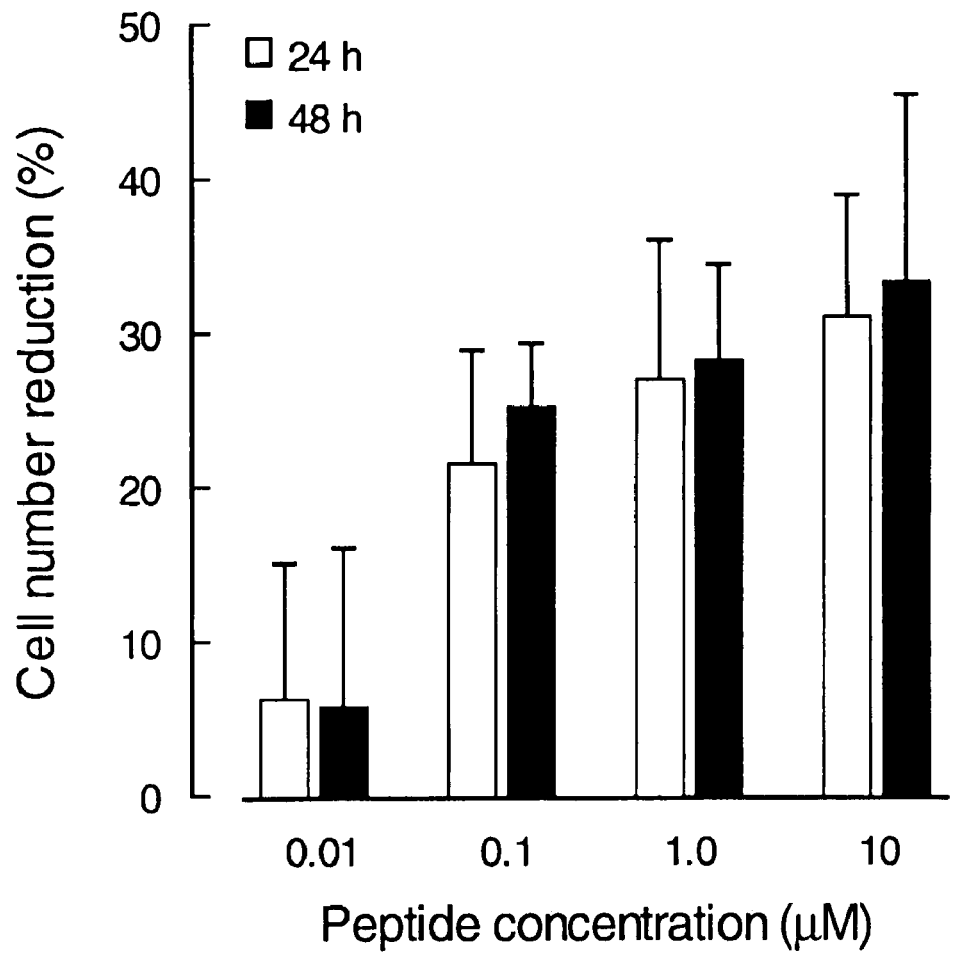
Figure 1. Effect on bovine mammary epithelial cells in culture of treatment with peptides A, B and C for up to 48 hours. Six experiments under varied culture conditions. Mean ±SEM.

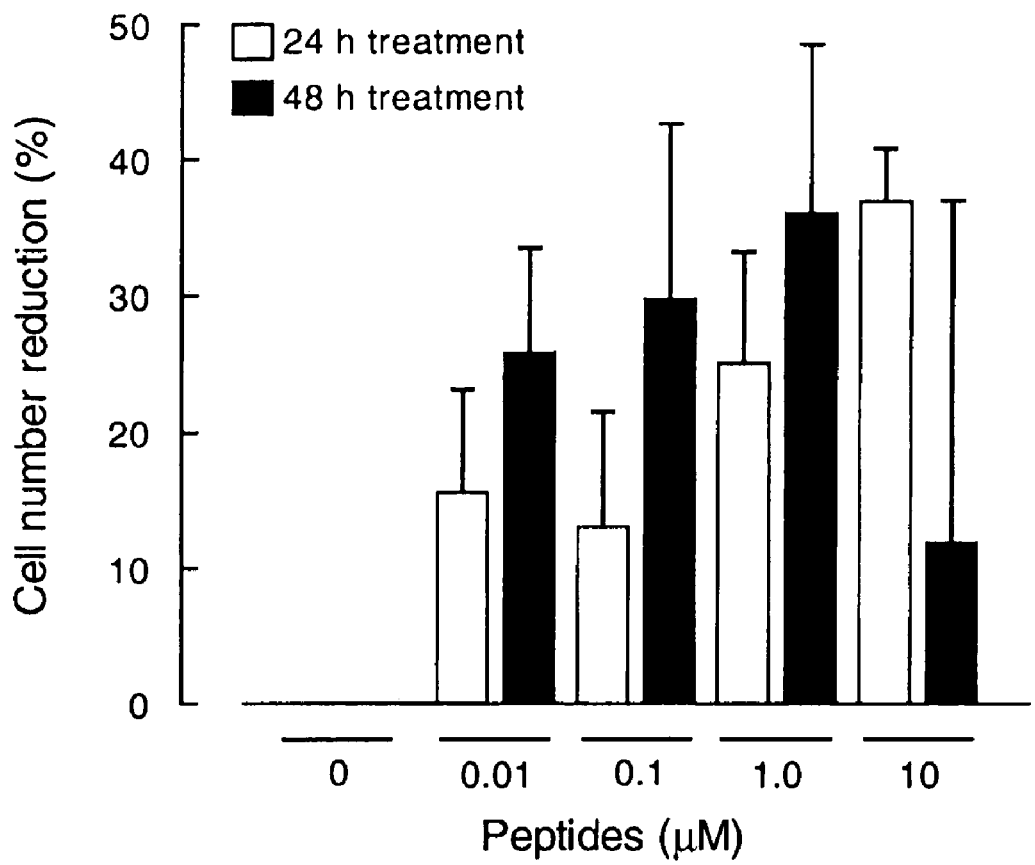
Figure 2. Effect on bovine mammary epithelial cells in culture of treatment with peptides A, B and C for up to 48 hours. Three experiments using cell from different animals. Mean ±SEM.

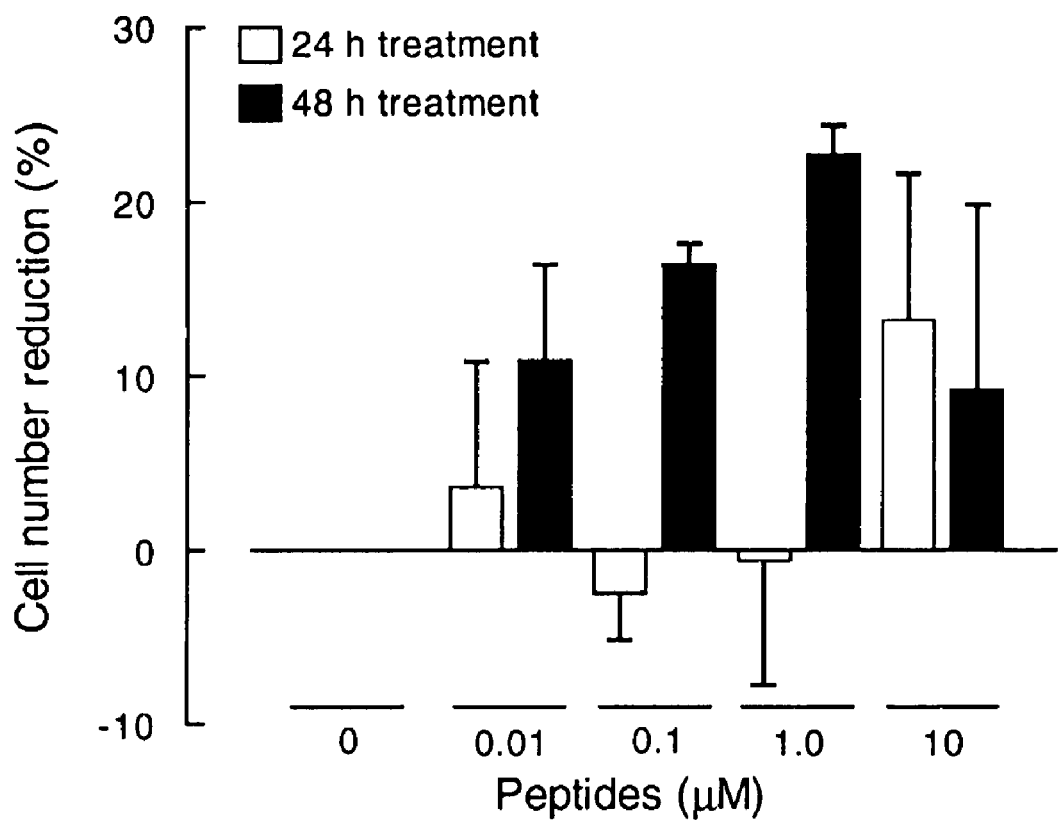
Figure 3. Effect of triple peptide treatment on MCF-7 human mammary tumour cell number. Five experiments. Mean ± SEM.

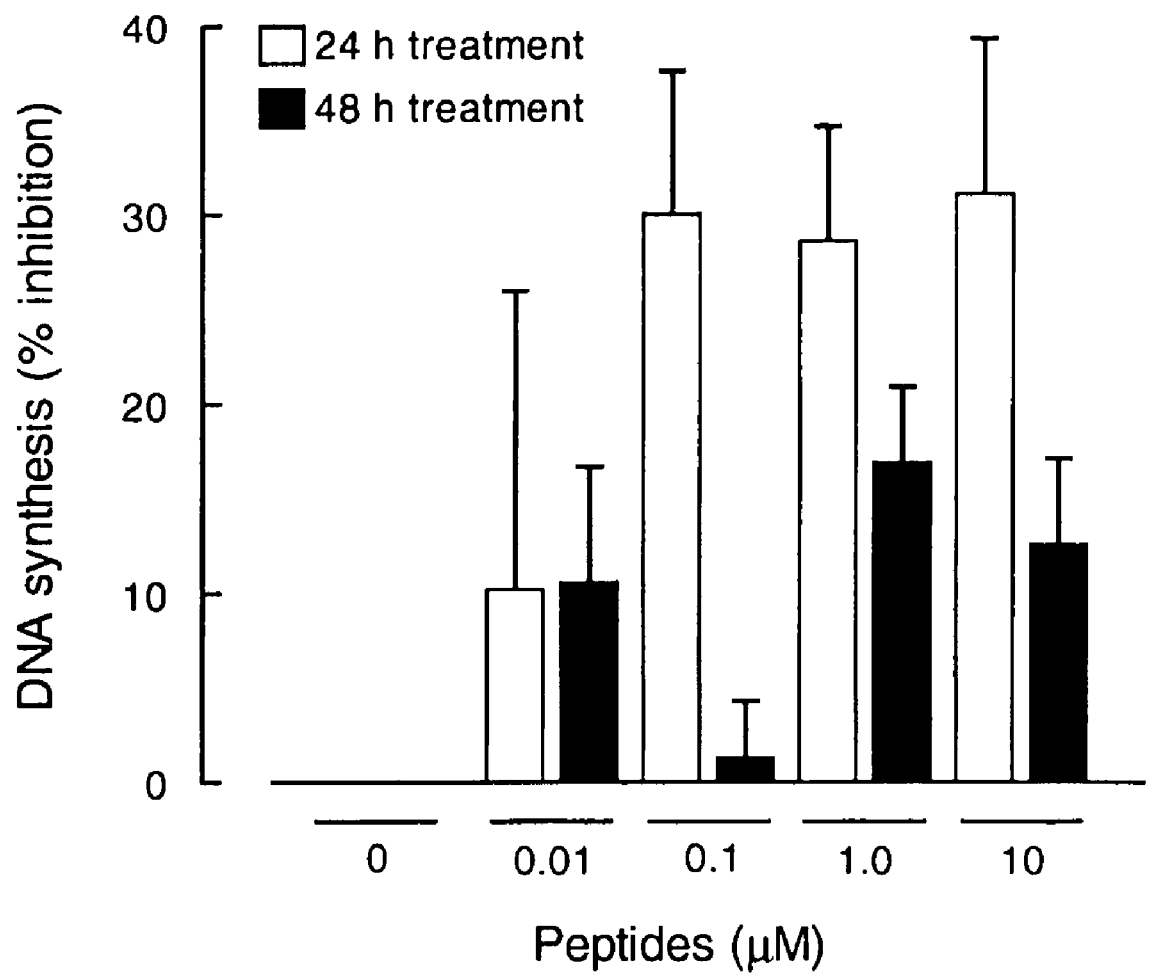
Figure 4. Effect of triple peptide treatment on MCF-7 human mammary tumour cell proliferation, measured as DNA synthesis by [$^3$H]-thymidine incorporation. Five experiments. Mean ± SEM.

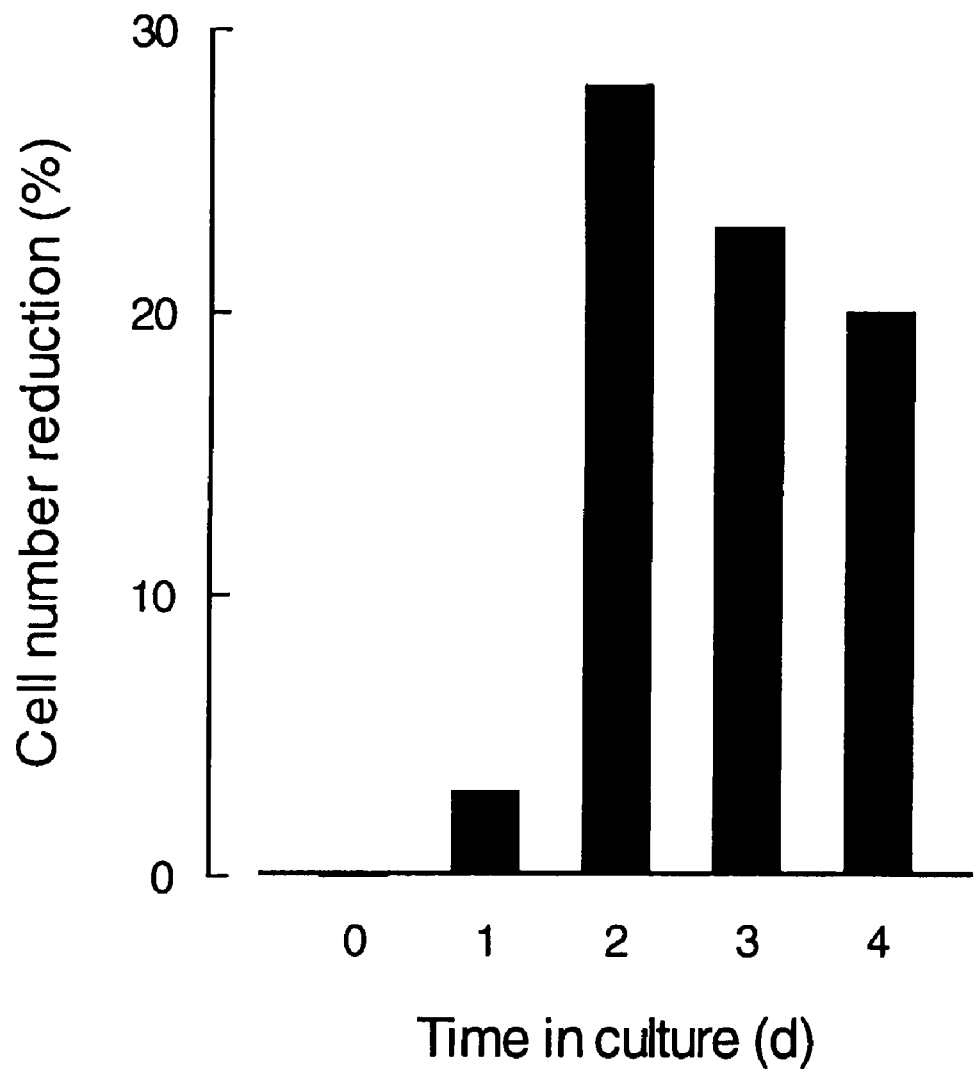
Figure 5. Time course of response to treatment of human tumour cell line MCF-7 with peptides A, B and C for up to 4 days, using a 1 μM concentration of each peptide.

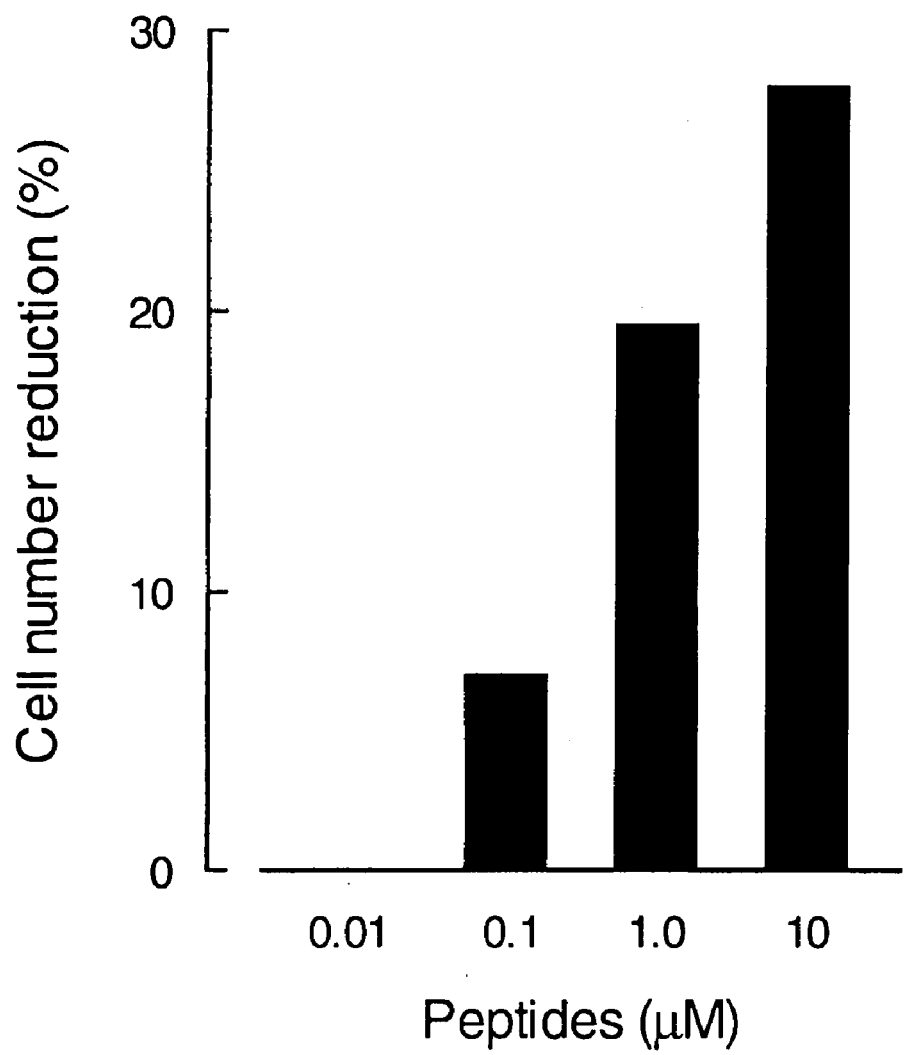
Figure 6. Effect on human mammary epithelial cell number of treatment with peptides A, B and C for 24 hours.

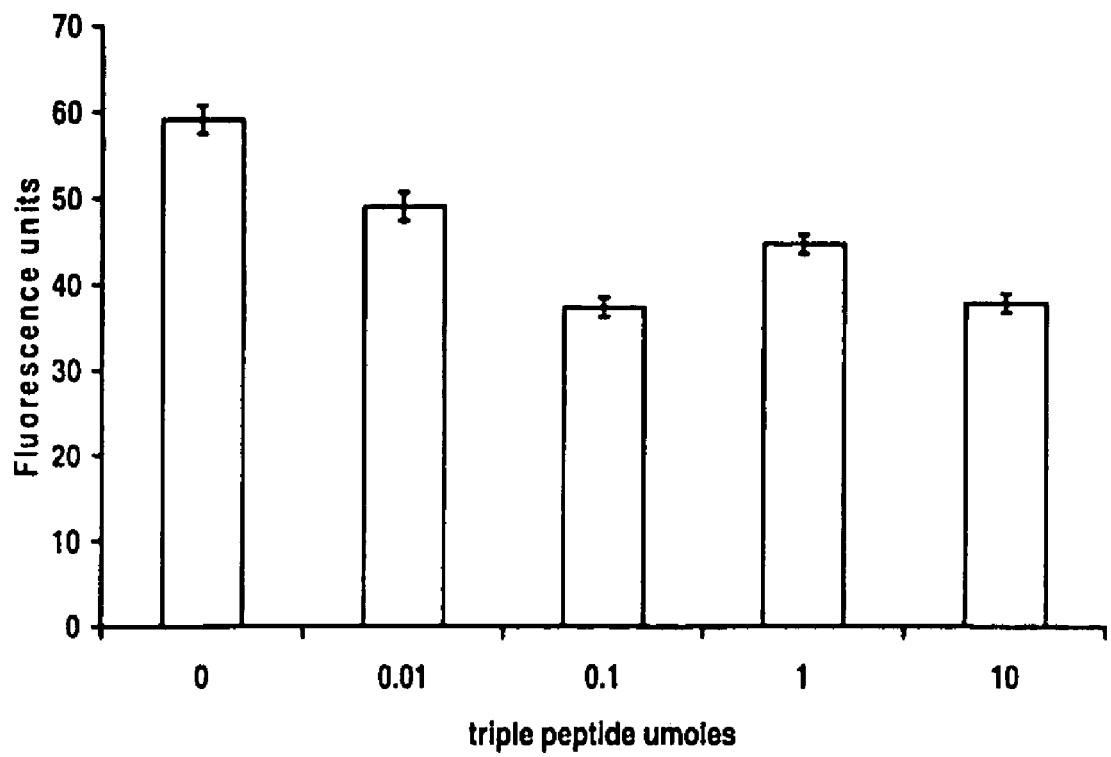
Figure 7. Effect of triple-peptide treatment on cell number in a human mammary cell culture.

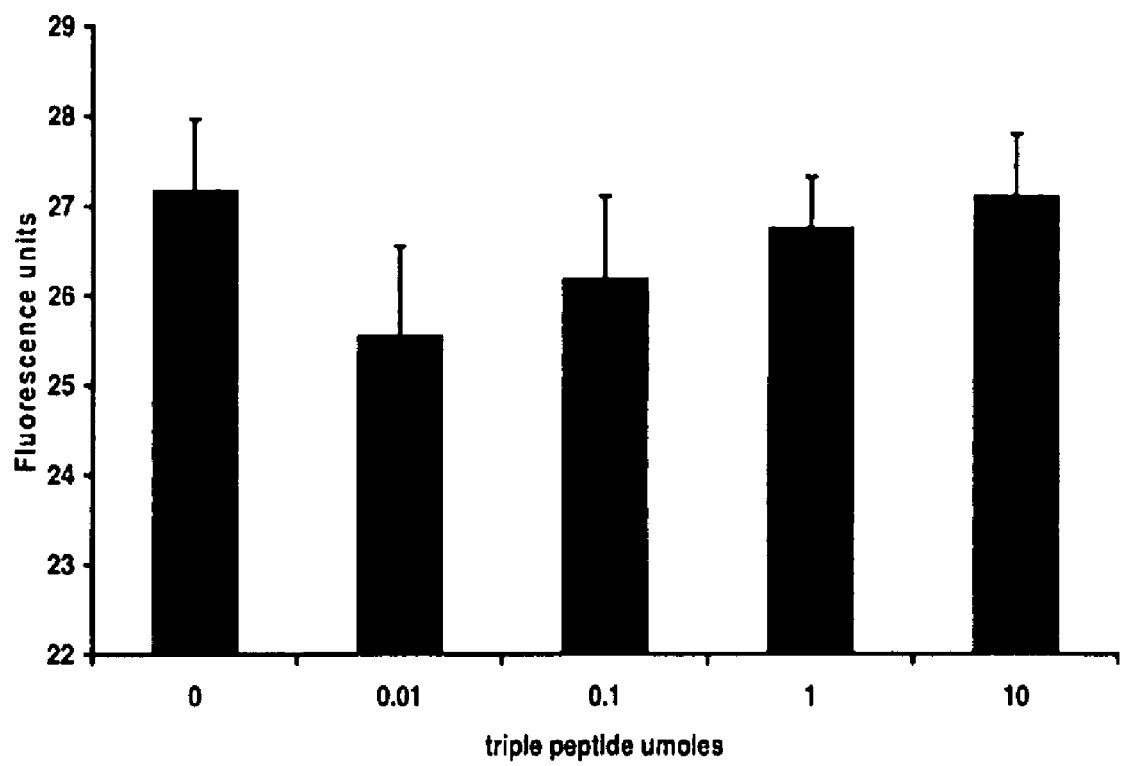
Figure 8. Effect of triple-peptide treatment on cell number in a human liver cell line.

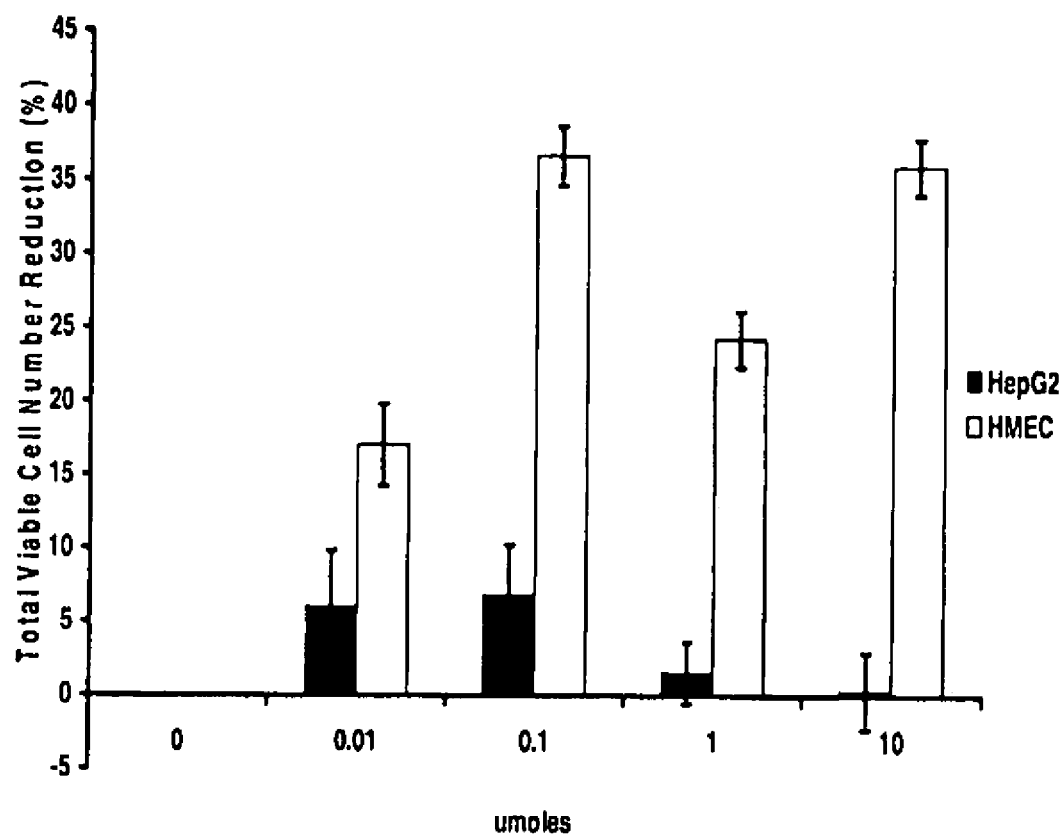
Figure 9. Reduction in human mammary and HepG2 cell number after 24 h treatment with milk-derived peptides.

COMPOSITIONS AND METHODS FOR THE CONTROL OF MAMMARY CELL NUMBER

FIELD OF INVENTION

The present invention relates to peptides for use in the control of cell number. The invention further extends to methods of controlling mammary cell number using said peptides and in particular to methods for the use of the peptides in the control of mammary (breast) cell number in mammals, including humans. The use of said peptides in the treatment of cancers for example breast cancer is further provided.

BACKGROUND OF THE INVENTION

Constituents of milk are known to control the rate of milk secretion and the extent of mammary development according to the frequency and completeness with which those constituents are removed through the demand of the offspring or the farmer's husbandry. Alternative methods of inducing milk secretion can be provided by mechanical means which reproduce the stimulus required to provide lactation. Such biochemical feedback mechanisms within the breast or udder act to modulate the lactation-promoting effects of mammogenic and galactopoietic hormones. The regulatory characteristics, albeit not all of the active factors in milk, have been described by studies on lactating ruminants at the Hannah Research Institute, Ayr, Scotland.

Mammary development, measured in terms of the number of parenchymal cells, is subject to control by local mechanisms activated by the frequency of milk removal during lactation. Circumstantial evidence obtained from milking studies in dairy animals suggests that this local control may also be regulated through feedback control by constituents of milk.

SUMMARY OF THE INVENTION

It has been shown that three peptides present in cow's milk, which can be purified from cow's milk by a series of chromatographic separation techniques, act to reduce mammary cell number.

The inventor of the present invention has now surprisingly shown that the peptides described herein can be used to effect a reduction in mammary cell number. The discovery that these peptides reduce mammary cell number further enables the use of these peptides in the treatment of cancer where the peptides can be used to reduce cell number and accordingly reduce or prevent tumour development. The inventor has further shown that the peptides have specific utility in the treatment of breast cancer.

According to a first aspect of the present invention there is provided a method for reducing mammary cell number comprising administering to a mammalian subject at least one peptide comprising the amino acid sequence RPKHPIKHQG (SEQ ID NO:1), AVAVSQEAN (SEQ ID NO:2) or SEGVALDPAR (SEQ ID NO:3) or an analogue, fragment, derivative, variant or mimetic thereof.

In one specific embodiment the peptide comprises the amino acid sequence of SEQ ID NO:2 or an analogue thereof.

In a preferred embodiment of the invention, the method comprises administration of at least 2 peptide selected from a peptide comprising the amino acid sequence RPKHPIKHQG (SEQ ID NO:1), a peptide comprising the amino acid sequence AVAVSQEAN (SEQ ID NO:2) or a peptide comprising the amino acid sequence SEGVALDPAR (SEQ ID NO:3) or analogues, fragments, derivatives, variants or mimetics thereof.

In a further specific embodiment the method comprises the administration of a peptide comprising the amino acid sequence of SEQ ID NO:2 or an analogue thereof in combination with at least one of a peptide comprising the amino acid sequence AVAVSQEAN (SEQ ID NO:2) or a peptide comprising the amino acid sequence SEGVALDPAR (SEQ ID NO:3) or analogues thereof.

In a yet further specific embodiment the method comprises the administration of a peptide comprising the amino acid sequence RPKHPIKHQG (SEQ ID NO:1), a peptide comprising the amino acid sequence AVAVSQEAN (SEQ ID NO:2) and a peptide comprising the amino acid sequence SEGVALDPAR (SEQ ID NO:3) or analogues thereof.

Although in preferred embodiments, a mixture of up to 3 peptides having the amino acid sequences defined in SEQ ID NO:1, 2 or 3 or analogues thereof is used, the peptides of the invention or analogues thereof may be used individually.

The term 'reducing mammary cell number' means preventing the formation or development of mammary cells through the process of cell division, or to reducing or slowing the formation of mammary cells through cell division.

In one embodiment the mammalian subject is any mammal which is capable of lactating. In a further embodiment, the mammal is a cow, goat, sheep or camelid. Alternatively the mammal is a human.

In a further aspect, the present invention provides a method for the treatment of cancer in a mammalian subject, comprising the steps of administering to the subject an effective amount of at least one peptide having the sequence RPKHPIKHQG (SEQ ID NO:1), AVAVSQEAN (SEQ ID NO:2) or SEGVALDPAR (SEQ ID NO:3) or an analogue, fragment, derivative, variant or mimetic thereof.

In one embodiment of the invention, an analogue of SEQ ID NO:2 of and for use in the invention may be the amino acid sequence of SEQ ID NO:4. This may be produced by adding a cysteine residue to the C-terminal sequence of the sequence of SEQ ID No 2, thus providing the sequence AVAVSQEANC (SEQ ID No 4).

A further analogue of and for use in the invention is RPKHPIKHQGLPEQV (SEQ ID NO:5) which is an analogue of SEQ ID NO:1.

In one embodiment of this aspect of the invention the cancer is breast cancer.

In a yet further aspect of the invention there is provided a composition comprising at least one peptide comprising the amino acid sequence RPKHPIKHQG (SEQ ID NO:1), at least one peptide comprising the amino acid sequence AVAVSQEAN (SEQ ID NO:2) or at least one peptide comprising the amino acid sequence SEGVALDPAR (SEQ ID NO:3) or analogues, fragments, derivatives, variants or mimetics thereof for use in the treatment of cancer.

In a preferred embodiment said composition comprises at least 2, most preferably 3 peptides selected from the peptides having the amino acid sequences of SEQ ID NO:1, SEQ ID NO:2, or SEQ ID NO:3.

In one specific embodiment the peptide comprises the amino acid sequence of SEQ ID NO:2 or an analogue thereof.

In a preferred embodiment of the invention, the method comprises administration of at least 2 peptides selected from a peptide comprising the amino acid sequence RPKHPIKHQG (SEQ ID NO:1), a peptide comprising the amino acid sequence AVAVSQEAN (SEQ ID NO:2) or a peptide comprising the amino acid sequence SEGVALDPAR (SEQ ID NO:3) or analogues, fragments, derivatives, variants or mimetics thereof.

In a further specific embodiment the method comprises the administration of a peptide comprising the amino acid sequence of SEQ ID NO:2 or an analogue thereof in combination with at least one of a peptide comprising the amino acid sequence AVAVSQEAN (SEQ ID NO:2) or a peptide comprising the amino acid sequence SEGVALDPAR (SEQ ID NO:3) or analogues thereof.

In one embodiment of this aspect of the invention the cancer is breast cancer.

In one embodiment the composition is administered to a mammal, preferably a human.

In a further aspect of the invention the present invention provides a peptide comprising the amino acid sequence RPKHPIKHQG (SEQ ID NO:1), or an analogue, fragment, derivative, variant or mimetic thereof for use in the inhibition of mammary cell number.

In a further aspect of the invention the present invention provides a peptide comprising the amino acid sequences AVAVSQEAN (SEQ ID NO:2), or an analogue, fragment, derivative, variant or mimetic thereof for use in the inhibition of mammary cell number.

In a further aspect of the invention the present invention provides a peptide comprising the amino acid sequences SEGVALDPAR (SEQ ID NO:3), or an analogue, fragment, derivative, variant or mimetic thereof for use in the inhibition of mammary cell number.

A further aspect of the present invention provides a pharmaceutical composition for the treatment of cancer, wherein the composition comprises a peptide mixture comprising at least one peptide comprising the amino acid sequence RPKHPIKHQG (SEQ ID NO:1), at least one peptide comprising the amino acid sequence AVAVSQEAN (SEQ ID NO:2) and at least one peptide comprising the amino acid sequence SEGVALDPAR (SEQ ID NO:3) or analogues, fragments, derivatives, variants or mimetics of said sequences along with a pharmaceutically acceptable excipient, diluent or carrier.

In a preferred embodiment of this aspect of the invention, the cancer is breast cancer.

The present invention further extends to peptides which are suitable for use in the present invention.

Accordingly, a further aspect of the present invention provides a peptide comprising the amino acid sequence RPKHPIKHQG (SEQ ID NO:1), AVAVSQEAN (SEQ ID NO:2) or SEGVALDPAR (SEQ ID NO:3) or an analogue, variant, fragment, mimetic or derivative thereof.

In one embodiment of this aspect of the invention the peptide is combined in a composition with at least one other of the two peptides including the amino acid sequence shown in SEQ ID NO:1, SEQ ID NO:2 or SEQ ID NO:3, such a composition reducing mammary cell number in animals, including humans.

In a further embodiment of this aspect of the invention the peptides comprise a composition comprising a mixture of peptides, wherein at least one peptide comprises the amino acid sequence RPKHPIKHQG (SEQ ID NO:1), at least one peptide comprises the amino acid sequence AVAVSQEAN (SEQ ID NO:2) and at least one peptide comprises the amino acid sequence SEGVALDPAR (SEQ ID NO:3) or analogues, fragments, derivatives, variants or mimetics of said sequences.

In a further embodiment the amino acid sequences shown in SEQ ID NO:1, SEQ ID NO: 2 and SEQ ID NO:3 are provided at the N-terminal sequence of each peptide.

In one embodiment the peptides of this aspect of the invention are isolated peptides.

As used herein, an "isolated" peptide is a peptide which is synthetic (e.g. recombinant), or which is altered, removed or purified from the natural state through human intervention.

In one embodiment the peptides can be co-purified from a 6-30 kDa fraction of whey protein of cowls milk with each of the other peptides including the amino acid sequence shown in SEQ ID NO:1, SEQ ID NO:2, SEQ ID NO:3, SEQ ID NO:4 or SEQ ID NO:5.

In particular, the peptides can be purified from cow's milk by a series of chromatographic separation techniques.

Specifically, when a 6-30 kDa fraction of cow's milk whey proteins is resolved by gel filtration on a cross-linked co-polymer of allyl dextran and N,N methylenebisacrylamide having an average particle size of 47 μm, such as Sephacryl S-100 (Pharmacia), the fourth-eluting component resolved by this method, "peak S4", comprises the peptides.

More specifically, the peptides are co-purified when a 6-30 kDa fraction of the cow's milk whey proteins is resolved by gel filtration on a cross-linked copolymer of allyl dextran and N,N methylenebisacrylamide having an average particle size of 47 μm, such as Sephacryl S-100 (Pharmacia). The fourth-eluting component resolved by this method, "peak S4", comprises the co-purified peptides.

When peak S4 is resolved further by peptide gel-filtration chromatography on a gel of dextran covalently bonded to highly cross-linked agarose beads with a mean diameter of 13-15 μm, such as Superdex Peptide HR (Pharmacia), the leading edge of the major eluted component eluting at 8-11.5 ml, designated P8-11A, contains the peptides. Further, when fraction P8-11A is resolved by reverse phase chromatography on a reversed phase column (Genesis 25 cm, C18 4 micron; Jones Chromatography), the fractions eluted after 34-36 minutes at a concentration of 36-39% acetonitrile, in a linear gradient of same in 0.1% trifluoroacetic acid, contains the peptides.

Analogues and Derivatives

The present invention extends to peptides which are derivates of homologs of the peptides of the invention, such peptides may have a sequence which has at least about 30%, or 40%, or 50%, or 60%, or 70%, or 75%, or 80%, or 85%, or 90%, 95%, 98% or 99% homology to the sequence of the peptides of the invention. Thus, a peptide fragment of any one of the peptides of the invention may include 1, 2, 3, 4, 5 or greater than 5 amino acid alterations. Such alterations may be provided at the N terminal, C terminal or at any other suitable point in the sequence of the peptide.

Moreover, or in addition, the peptide may consist of a truncated version of the peptides of the invention which has been truncated by 1, 2, 3, 4 or 5 amino acids.

The percent identity of two amino acid sequences or of two nucleic acid sequences may be determined by aligning the sequences for optimal comparison purposes (e.g. gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those skilled in the art. The NBLAST and XBLAST programs are examples of computer programs which perform such algorithms. BLAST nucleotide searches can be performed with the NBLAST program to obtain nucleotide sequences homologous to nucleic acid molecules of the invention. BLAST protein searches can be performed with the XBLAST program to obtain amino acid sequences homologous to protein molecules of the invention.

To obtain gapped alignments for comparison purposes, Gapped BLAST can be utilised. Alternatively, PSI-Blast can be used to perform an iterated search which detects distant relationships between molecules (Idem.). When utilising BLAST, Gapped BLAST, and PSI-Blast programs, the default parameters of the respective programs (e.g., XBLAST and NBLAST) can be used. See URL http://www.ncbi.nlm.nih.gov.

Further suitable computer based algorithm programs can be utilised and will be known to the person skilled in the art.

A derivative of a peptide for which the specific amino acid sequence is disclosed herein may be in certain embodiments the same length or shorter than the specific peptide. In other embodiments, the peptide sequence or a variant thereof may include a larger peptide.

As is well understood, homology at the amino acid level is generally in terms of amino acid similarity or identity. Similarity allows for 'conservative variation', such as substitution of one hydrophobic residue such as isoleucine, valine, leucine or methionine for another, or the substitution of one polar residue for another, such as lysine or glutamic acid for aspartic acid, or glutamine for asparagine.

Analogues of, and for use in, the invention as defined herein means a peptide modified by varying the amino acid sequence e.g. by manipulation of the nucleic acid encoding the protein or by altering the protein itself. Such derivatives of the amino acid sequence may involve insertion, addition, deletion and/or substitution of one or more amino acids, while providing a peptide capable of inducing a reduction in mammary cell number, either on its own, or in combination with other peptides.

Analogues also include derivatives of the defined peptides, including the peptide being linked to a coupling partner, e.g. an effector molecule, a label, a drug, a toxin and/or a carrier or transport molecule. Techniques for coupling the peptides of the invention to both peptidyl and non-peptidyl coupling partners are well known in the art.

Analogues also include derivatives of the defined peptides, including the peptide being linked to a coupling partner, e.g. an effector molecule, a label, a drug, a toxin and/or a carrier, targeting or transport molecule. Techniques for coupling the peptides of the invention to both peptidyl and non-peptidyl coupling partners are well known in the art.

Non-peptide mimetics are further provided within the scope of the invention. Peptides according to the invention may be prepared, either wholly or partly, by chemical synthesis. Generation of the peptides in this way can be performed by methods which are well known to the person skilled in the art of the present invention, particularly standard liquid or solid-phase peptide synthesis methods. Another way of producing the peptides according to the invention is to express the nucleic acid encoding the amino acid sequences in a nucleic acid expression system.

According to a further aspect of the present invention, there is provided a peptide comprising the amino acid sequence of SEQ ID NO:1, SEQ ID NO:2 or SEQ ID NO:3, which in combination with one or more further peptides comprising the amino acid sequence shown SEQ ID NO:1, SEQ ID NO:2 or SEQ ID NO:3 provides a reduction in mammary cell number in a mammal.

In a specific embodiment the composition comprises the administration of a peptide comprising the amino acid sequence of SEQ ID NO:2 or an analogue thereof in combination with at least one of a peptide comprising the amino acid sequence AVAVSQEAN (SEQ ID NO:2) or a peptide comprising the amino acid sequence SEGVALDPAR (SEQ ID NO:3) or analogues thereof.

In one embodiment the mammal is a human.

In one preferred embodiment, the peptide comprises the amino acid sequence shown in SEQ ID NO:1 or an analogue, fragment, derivative, variant or mimetic thereof.

In another preferred embodiment, the peptide comprises the amino acid sequence shown in SEQ ID NO:2 or an analogue, fragment, derivative, variant or mimetic thereof.

In a yet further preferred embodiment, the peptide comprises the amino acid sequence shown in SEQ ID NO:3 or an analogue, fragment, derivative, variant or mimetic thereof.

Preferably the peptide has a molecular mass determined by mass spectrometric analysis of between 1000 to 3000 Da.

In a particular embodiment of the invention, the peptide is glycosylated. Alternatively the peptide is unglycosylated.

Further, the peptides of the present invention can be in either phosphorylated or unphosphorylated form.

The peptides of the invention may further be subjected to any other relevant form of post-translational modification such as sulfation, acetylation, ribosylation, deamination and cleavage.

The present invention further includes truncated versions of the peptides which have been isolated from mammalian milk, and in particular, cow's milk.

A further aspect of the invention provides a peptide mixture comprising two or more different peptides, the peptides including the amino acid sequence of SEQ ID NO:1, SEQ ID NO:2 or SEQ ID NO:3, or analogues thereof for use in the reduction of mammary cell number in a mammal.

In one embodiment the mammalian subject is any mammal which is capable of lactating. In a further embodiment, the mammal is a cow, goat, sheep or camelid. Alternatively the mammal is a human.

Suitable methods of administration will be known to the person skilled in the art. Such methods include intravenous, intra-mammary, subcutaneous, and intra-ductal through the teat into the mammary milk storage space.

A yet further aspect of the present invention provides for antibodies directed to a peptide comprising, for example, the amino acid sequence RPKHPIKHQG (SEQ ID NO:1), AVAVSQEAN (SEQ ID NO:2) or SEGVALDPAR (SEQ ID NO:3) or an analogue thereof.

In one embodiment said antibodies result in an increase of mammary cell number in humans and other mammals.

Preferably said antibodies modulate the cell division rate of mammary cells of animals, most preferably humans, sheep, cows and goats. Without wishing to be bound by theory, it is believed that the antibodies act through inhibiting the action of peptides which include the amino acid sequence shown in SEQ ID NO:1, SEQ ID NO:2 or SEQ ID NO:3, such peptides having a role in the reduction of mammary cell number.

An "antibody" is an immunoglobulin, whether natural or partly or wholly synthetically produced. The term also covers any polypeptide, protein or peptide having a binding domain which is, or is homologous to, an antibody binding domain. These can be derived from natural sources, or they may be partly or wholly synthetically produced. Examples of antibodies are the immunoglobulin isotypes and their isotypic subclasses as well as fragments which comprise an antigen binding domain.

The binding member of the invention may be an antibody such as a monoclonal or polyclonal antibody, or a fragment thereof. The constant region of the antibody may be of any class including, but not limited to, human classes IgG, IgA, IgM, IgD and IgE. The antibody may belong to any subclass e.g. IgG1, IgG2, IgG3 and IgG4.

As antibodies can be modified in a number of ways, the term "antibody" should be construed as covering any binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies is described in EP-A-0120694 and EP-A-0125023.

It has been shown that fragments of a whole antibody can perform the function of antigen binding.

Examples of such binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site; (viii) bispecific single chain Fv dimers and (ix) "diabodies", multivalent or multispecific fragments constructed by gene.

The term "antibody" includes antibodies which have been "humanised". Methods for making humanised antibodies are known in the art. Methods are described, for example, in Winter, U.S. Pat. No. 5,225,539.

In an alternative embodiment, inhibition of the action of a peptide or peptides including the amino acid sequence shown in SEQ ID NO:1, SEQ ID NO:2 or SEQ ID NO:3 can be effected by a small molecule which inhibits the biological function of the peptide, or further by down-regulation of a gene encoding a peptide or more generally for genes encoding the peptides of the present invention. Assay methods for assessing the effectiveness of small molecules as inhibitors of the peptides of the present invention are also within the scope of the present invention.

A yet further aspect of the present invention provides a composition for reducing mammary cell numbers in mammals, the composition including a peptide including the amino acid sequence RPKHPIKHQG (SEQ ID NO:1), AVAVSQEAN (SEQ ID NO:2) or SEGVALDPAR (SEQ ID NO:3) or an analogue thereof.

As used herein the term 'mammal' includes all mammals which are capable of lactating. Preferably the mammal is human. Alternatively the mammal may be non-human, such as a cow, goat or sheep.

In one embodiment the composition inhibits cell division of mammary gland cells within a time period of hours (for example 1 to 36 hours, preferably 1 to 24 hours and most preferably 1 to 12 hours) of administration.

In one embodiment the composition is administered by intra-ductal injection into the mammary gland at a dose level yielding a final concentration of peptides in milk in the range 0.1 to 16 micromolar. The administration of this dose may be repeated as required, and possibly increased when given over long periods.

A yet further aspect of the present invention provides a method of reducing mammary cell number in a mammal, the method comprising the steps of:

selecting a composition including at least one peptide including the amino acid sequence RPKHPIKHQG (SEQ ID NO:1), AVAVSQEAN (SEQ ID NO:2) or SEGVALDPAR (SEQ ID NO:3) or an analogue thereof, administering the composition to the animal through local targeting of the mammary cells, such that the cells of the mammary gland are exposed to a concentration of the composition sufficient to result in a decrease in mammary cell number.

In one embodiment this composition is a pharmaceutic which can be administered in order to reduce mammary cell number.

In a particularly preferred embodiment of this aspect of the invention, the composition, which is preferably a pharmaceutic, can be used to reduce mammary tumour cell number.

In one embodiment the composition is administered through intraductal administration.

In one embodiment the delivery of the composition is by means of a bolus of peptide which is preferably encapsulated.

Preferably the encapsulation material is a non-phosphate containing isotonic buffer at the physiological pH of milk i.e. pH 6.7.

Pharmaceutic and Pharmaceutical Compositions

As described above, the present invention extends to pharmaceutics, pharmaceutic compositions and to pharmaceutical compositions for the reduction of mammary cell number and in particular for the treatment of cancers such as breast cancer, wherein the composition comprises at least one peptide having the sequence defined in SEQ ID NO:1, SEQ ID NO:2, SEQ ID NO:3, SEQ ID NO:4 or SEQ ID NO:5. Pharmaceutical compositions according to the present invention, and for use in accordance with the present invention may comprise, in addition to active ingredient (i.e. one or more peptides), a pharmaceutically acceptable excipient, carrier, buffer stabiliser or other materials well known to those skilled in the art. Such materials should be non-toxic and should not interfere with the efficacy of the active ingredient. The precise nature of the carrier or other material will depend on the route of administration, which may be, for example intravenous, sub-cutaneous, intra-mammary, or intra-ductal through the teat into the mammary milkstorage space.

The formulation may be a liquid, for example, a physiologic salt solution containing non-phosphate buffer at pH 6.7 to 7.6 when the peptides are administered systemically or into the mammary teat duct. For intra-mammary administration by injection into the gland, the preferred formulation is an oil-based formulation, preferably using mineral oil.

Dose

The composition is preferably administered to an individual in a "therapeutically effective amount", this being sufficient to show benefit to the person or animal to whom the composition is administered.

The actual amount of composition administered, as well as the rate and time-course of administration, will depend on the nature of the animal being treated.

The optimal dose can be determined based on a number of parameters including, for example, animal type, age and stage through lactation, the precise form of the composition being administered and the route of administration.

The composition may be administered via microspheres, liposomes, other microparticulate delivery systems or sustained release formulations placed in certain tissues including blood. Suitable examples of sustained release carriers include semipermeable polymer matrices in the form of shared articles, e.g. suppositories or microcapsules. Implantable or microcapsular sustained release matrices include polylactides (U.S. Pat. No. 3,773,919 and European Patent Application Publication No 0,058,481) copolymers of L-glutamic acid and gamma ethyl-L-glutamate (Sidman et al., Biopolymers 22(1): 547-556, 1985), poly (2-hydroxyethyl-methacrylate) or ethylene vinyl acetate (Langer et al., J. Biomed. Mater. Res. 15: 167-277, 1981, and Langer, Chem. Tech. 12:98-105, 1982, the entire disclosures of which are herein incorporated by reference).

Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, H. C. et al. 7$^{th}$ Edition ISBN 0-683305-72-7 the entire disclosures of which is herein incorporated by reference.

A yet further aspect of the present invention provides a method of treating breast cancer, the method comprising the steps of:
    selecting a composition including at least one peptide including the amino acid sequence RPKHPIKHQG (SEQ ID NO:1), AVAVSQEAN (SEQ ID NO:2) or SEGVALDPAR (SEQ ID NO:3) or an analogue thereof,
    administering a therapeutically useful amount of the composition to a subject in need of treatment through the local targeting of the mammary cells.

In one embodiment a therapeutically useful amount of the composition results in the cells of the mammary gland being exposed to a concentration of the composition sufficient to result in a decrease in mammary cell number.

A yet further aspect of the present invention provides for the use of at least one peptide including the amino acid sequence RPKHPIKHQG (SEQ ID NO:1), AVAVSQEAN (SEQ ID NO:2) or SEGVALDPAR (SEQ ID NO:3) or an analogue thereof in the treatment of breast cancer.

A yet further aspect of the present invention provides for the use of at least one peptide including the amino acid sequence RPKHPIKHQG (SEQ ID NO:1), AVAVSQEAN (SEQ ID NO:2) or SEGVALDPAR (SEQ ID NO:3) or an analogue thereof in the preparation of a composition for the treatment of breast cancer.

Treatment

The term 'treatment' is used herein to refer to any regime that can benefit a human or non-human animal. The treatment may be in respect of an existing condition or may be prophylactic (preventative treatment). Treatment may include curative, alleviation or prophylactic effects.

More specifically, reference herein to "therapeutic" and "prophylactic" treatment is to be considered in its broadest context. The term "therapeutic" does not necessarily imply that a subject is treated until total recovery. Similarly, "prophylactic" does not necessarily mean that the subject will not eventually contract a disease condition.

Accordingly, therapeutic and prophylactic treatment includes amelioration of the symptoms of a particular condition or preventing or otherwise reducing the risk of developing a particular condition. The term "prophylactic" may be considered as reducing the severity or the onset of a particular condition. "Therapeutic" may also reduce the severity of an existing condition.

"Treatment of cancer" includes treatment of conditions caused by cancerous growth and includes the treatment of neoplastic growths or tumours. Examples of tumours that can be treated by the system of the invention are, for example; sarcomas, including osteogenic and soft tissue sarcomas, carcinomas, e.g. breast-, lung-, bladder-, thyroid-, prostate-, colon-, rectum-, pancreas-, stomach-, liver-, uterine-, cervical and ovarian carcinoma, lymphomas, including Hodgkin and non-Hodgkin lymphomas, neuroblastoma, melanoma, myeloma, Wilms tumor, and leukemias, including acute lymphoblastic leukaemia and acute myeloblastic leukaemia, gliomas and retinoblastomas.

The peptides of the present invention may be particularly useful in the treatment of breast cancers.

The compositions and peptides of the invention may be particularly useful in the treatment of existing cancer(s) and in the prevention of the recurrence of cancer after initial treatment, therapy or surgery.

The peptides according to the present invention may be used in screening for molecules which affect or modulate activity or function of the peptides. The interaction of such molecules with the peptides may be useful in a therapeutic and prophylactic context.

It is well known that pharmaceutical research leading to the identification of a new drug may involve the screening of a very large number of candidate substances, both before and even after a lead compound has been found. Such means for screening for substances potentially useful in treating or preventing cancer and in particular, breast cancer is provided by the peptides according to the present invention. Substances identified as modulators of the polypeptide represent an advance in the therapy in these areas as they provide basis for design and investigation of therapeutics for in vivo use.

In various further aspects, the present invention relates to screening and assay methods and to substances identified thereby.

Thus, a further aspect of the present invention provides the use of a peptide (including a fragment or derivative thereof) of the invention in screening or searching for and/or obtaining or identifying a substance such as a peptide or chemical compound which interacts with or binds with the peptide of the invention and/or interferes with its biological function or activity or that of another substance. For instance, a method according to one aspect of the present invention includes providing a peptide of the invention and bringing it into contact with a substance, which contact may result in binding between the peptide and the substance. Binding may be determined by any number of techniques, both qualitative and quantitative which would be known to the person skilled in the art.

A substance identified as a modulator of peptide function may be a peptide or non-peptide in nature. Non-peptide "small molecules" are often preferred for many in-vivo pharmaceutical uses. Accordingly, a mimetic or mimic of the substance may be designed for pharmaceutical uses. The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that ate critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been determined, its structure is modelled according to its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can also be used in this modelling process.

In a variant of this approach, the three-dimensional structure of the ligand and its binding partner are modelled. This can be especially useful where the ligand and/or binding partner change conformation on binding, allowing the model to take account of the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in-vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in-vivo or clinical testing.

A further aspect of the present invention therefore provides an assay for assessing binding activity between at least one peptide of the invention and a putative binding molecule which comprises the steps of:
bringing at least one peptide into contact with a putative binding molecule or other test substance, and
determining interaction or binding between the at least one peptide and the binding molecule or test surface,
wherein binding between the at least one peptide and the binding molecule is indicative of the utility of the at least one peptide.

A substance which interacts with the peptide of the present invention may be isolated and/or purified, manufactured and/or used to modulate its activity.

It is not necessary to use the entire peptide of the invention for assays of the invention which test for binding between two molecules. Fragments may be generated and used in any suitable way known to the person skilled in the art.

Further, the precise format of the assay of the invention may be varied by those skilled in the art using routine skill and knowledge.

A yet further aspect of the invention provides the use of a ligand directed to a peptide including the amino acid sequence RPKHPIKHQG (SEQ ID NO:1), AVAVSQEAN (SEQ ID NO:2) or SEGVALDPAR (SEQ ID NO:3) or an analogue thereof for use as a drug target in the preparation of a medicament for the treatment of mammary or breast cancer.

In a still further aspect of the present invention there is provided a kit for the performance of any one of the assay methods of the invention, said kit comprising at least one peptide according to the invention together with instructions and protocols for the performance of the method(s).

Preferred features and embodiments of each aspect of the invention are as for each of the other aspects mutatis mutandis unless the context demands otherwise.

Unless otherwise defined, all technical and scientific terms used herein have the meaning commonly understood by a person who is skilled in the art in the field of the present invention.

Throughout the specification, unless the context demands otherwise, the terms 'comprise' or 'include', or variations such as 'comprises' or 'comprising', 'includes' or 'including' will be understood to imply the inclusion of a stated integer or group of integers, but not the exclusion of any other integer or group of integers.

BRIEF DESCRIPTION OF THE DRAWINGS AND DETAILED DESCRIPTION

The present invention will now be described with reference to the following examples which are provided for the purpose of illustration and are not intended to be construed as being limiting on the present invention. Reference will further be made to the accompanying drawings in which:

FIG. 1 shows results of experimentation showing the effect of treatment for up to 48 hours with peptides A, B and C on bovine mammary epithelial cells cultured under a variety of culture conditions (Mean±SEM), FIG. 2 shows results of experimentation showing the effect of treatment for up to 48 hours with peptides A, B and C on bovine mammary epithelial cells in culture, when cells were obtained from three different animals (Mean±SEM), FIG. 3 shows the effect of triple peptide treatment of human mammary tumour cell line MCF-7 with peptides A, B and C on viable cell number in culture (Mean±SEM), FIG. 4 shows the effect of triple peptide treatment with peptides A, B and C on cell proliferation of human mammary tumour cell line MCF-7 in culture, measured as DNA synthesis by [$^3$H]-thymidine incorporation (Mean±SEM), FIG. 5 shows a time course of response to treatment of human mammary tumour cell line MCF-7 with peptides A, B and C for up to 4 days using a defined concentration (1 µM) of each peptide, FIG. 6 shows the effect on cell number of treatment of normal human mammary epithelial cells with peptides A, B and C for 24 hours, FIG. 7 shows the effect of triple-peptide treatment on cell number in a human mammary cell culture, FIG. 8 shows the effect of triple-peptide treatment on cell number in a human liver cell line, and FIG. 9 shows a reduction in human mammary and HepG2 cell number after 24 hours of treatment with milk-derived peptides.

EXAMPLE 1

Experiments Using Bovine Mammary Epithelial Cells

Experimental Protocol

Experiments were undertaken using bovine mammary epithelial cells isolated from tissue of a late-pregnant animal. Cells were seeded into 24 well plates at a density of ~1×10$^4$ cells/cm$^2$, and were allowed to attach and grow for 3 days before use. In some cases cell attachment was promoted by pre-coating plates with gelatin.

Cells were then treated for up to 2 days with the three peptides A, B and C. Peptide A was a 15-residue peptide based on the published amino acid sequence of the N-terminus of $\alpha_{S1}$-casein (Lahov E & Regelson W. Food Chemistry and toxicology 34: 131-145). Peptides B and C were 10 and 10-residue peptides respectively based on the N-terminal sequences determined by Edman degradation with the C-ter minal addition of a cysteine residue to peptide B in order to facilitate the attachment of this peptide to the solid phase. Peptide sequences were:

```
Peptide A:         RPKHPIKHQGLPEQV
Peptide B:         AVAVSQEANC
Peptide C:         SEGVALDPAR
```

The peptides were tested at equimolar concentrations.

Medium was changed daily, and viable cell number was assayed using the fluorescence-based CellTiter Blue™ method (Promega UK, Southampton, UK). Results were compared with untreated control wells in each experiment.

Results

In six experiments, the number of viable bovine mammary epithelial cells was consistently lower in wells treated with the combination of three peptides (FIG. 1). This effect was statistically significant (P<0.001). The peptides' effect was realised rapidly, within 24 hours of addition to culture wells, and was concentration-dependent: the lowest concentration of 0.01 μM had little effect, but concentrations of 0.1 μM and greater caused a marked (>25%) reduction in cell number. In one of six experiments, cells were cultured without use of gelatin to assist cell anchorage. In this experiment, the peptides' effect was greatest, suggesting either that gelatin treatment of culture wells may have interfered with the assay, or that cells were more susceptible to the peptides if anchorage to the substratum was weakened.

EXAMPLE 2

Peptide Treatment of Bovine Mammary Epithelial Cells

The peptides' effect was seen consistently in cell preparations isolated from three different cows and cultured under the same experimental conditions, with a starting cell density of $0.4$-$1.0 \times 10^4/cm^2$ (FIG. 2). Of these three experiments, two were conducted using peptide B with a C-terminal cysteine residue added (peptide B(ii)), and one used peptide B without a C-terminal cysteine added (peptide B(i)).

Peptide sequences were:

```
Peptide A:         RPKHPIKHQGLPEQV
Peptide B (i):     AVAVSQEAN
Peptide B (ii):    AVAVSQEANC (with C terminal
                   cysteine residue
Peptide C:         SEGVALDPAR
```

EXAMPLE 3

Experiments Using Human Mammary Tumour Cell Line MCF-7

A human mammary tumour cell line MCF-7 was treated with combinations of peptides A, B and C at equal concentrations. Cells were seeded into 24 well plates at a starting density of ~$0.25$-$2.0 \times 10^4$ cells/cm$^2$ and were allowed to attach and grow for 3 days before use. In one experiment, peptide treatment was as described in Example 1. In all other experiments, the C-terminal cysteine residue (C) was omitted from peptide B. Other experimental conditions were the same as in Example 1.

Peptide sequences were therefore:

```
Peptide A:         RPKHPIKHQGLPEQV
Peptide B:         AVAVSQEANC
Peptide C:         SEGVALDPAR
```

The combination of three peptides A, B and C defined in Example 1 reduced viable cell number after 48 hours of treatment (FIG. 3). The results shown in FIG. 3 are from 5 experiments in which culture conditions were similar to those in Example 1, and cell number at start of treatment varied between experiments.

EXAMPLE 4

Experimental conditions were similar to those described in Example 3, and DNA synthesis was measured as the incorporation of TCA-precipitable radioactivity after culture in the presence of [3H]thymidine (5 μCi/ml culture medium) for the final 6 hours of culture. All experiments used a nine-residue peptide B with no C-terminal cysteine.

Treatment with peptides A, B and C also resulted in a reduction in DNA synthesis in MCF-7 cells in culture (FIG. 4). The reduction in DNA synthesis was evident after 24 hours treatment with peptides, preceded an effect on viable cell number, and was concentration-dependent and statistically significant (P<0.002). A concentration of 0.01 μM had little effect, but concentrations of 0.1-1.0 μM caused a marked reduction in DNA synthesis (>25%) after 24 and 48 hours, with equal concentrations of >0.1 μM peptide producing a sustained effect.

EXAMPLE 5

Experiments Using Human Tumour Cell Line MCF-7

This assay used peptide B with the addition of a C-terminal cysteine. When peptide treatment of MCF-7 human mammary tumour cells was continued for up to four days, a reduction in tumour cell number was evident throughout. These results are shown in FIG. 5.

EXAMPLE 6

Experiments Using Human Mammary Cells

Experiments were conducted using human mammary epithelial cells purchased from a commercial supplier (Cambrex Bioscience Ltd., Wokingham, UK). Cells were seeded into 24-well plates at a density of $2.5 \times 10^3/cm^2$, and were allowed to attach and grow for 3 days. Cells were then treated for up to 4 days with the three peptides which were prepared as in accordance with the guidance provided in Example 1. These assays used peptide B with the addition of a C-terminal cysteine. Peptide sequences were therefore:

```
Peptide A:         RPKHPIKHQGLPEQV
Peptide B:         AVAVSQEANC
Peptide C:         SEGVALDPAR
```

Medium was changed each day, at which time viable cell number was assayed using the fluorescence-based CellTiter Blue™ method (Promega UK, Southampton, UK).

Results were compared with untreated control wells in each experiment.

The three peptides in combination produced a concentration-dependent decrease in viable cell number within 24 hours of addition to the culture medium (FIG. 6).

EXAMPLE 7

Assessment of Specificity of Peptides to Mammary Cell Lines

The present example provides a comparison of the effect of the peptides of the invention on human mammary cells and a human non-mammary cell line, the liver-derived HepG2 cell line.

Experimental Protocol

Experiments were undertaken using Human Mammary Epithelial Cells (Clonetics) and a Human Hepatocyte Carcinoma cell line (European Collection of Cell Cultures). Hepatocytes represented a non-mammary cell type in which to compare the effects of peptides. Cells were seeded into 96 well plates at a density of 1000 cells/well and were allowed to attach and grow for 2 days before use. For HEPG2 cells, cell attachment was promoted by pre-coating plates with polylysine.

Cells were treated for 1 day with the three peptides 2 days after cell seeding. Peptide A was a 15-residue peptide based on the published amino acid sequence of the N-terminus of $\alpha_{S1}$-casein (Lahov E. and Regelson W. Food Chemistry and Toxicology 34:131-145). Peptides B and C were 9 and 10-residue peptides, respectively.

Peptide sequences were:

```
Peptide A:      RPKHPIKHQGLPEQV

Peptide B:      AVAVSQEAN

Peptide C:      SEGVALDPAR
```

The peptides were tested at equimolar concentrations.

Determination of Total Cell Number

Medium was changed upon the addition of peptides and total viable cell number was assayed using the fluorescence-based CellTiter Blue™ method (Promega U.K., Southampton) in the presence of reagent for the final 4 hour period within the 24 hour window when cells were exposed to peptides. Results were compared with untreated control wells in each experiment and 8 replicates were used for each experimental condition.

Description of the Data

The data describe the effect of a range of concentrations of the peptides on cell number, which is measured by a fluorimetric method. The assay is conducted in 96-well culture plates, such that all treatments are tested within a single assay. Peptides were tested at equimolar concentrations and treatment was for 24 h.

The peptide tended to reduce human mammary cell number in a concentration-dependent manner. The effect was statistically significant ($P<0.001$ for all treatments).

Treatment of HepG2 cells for 24 h did not significantly affect cell number. None of the differences compared with control cultures was statistically significant ($P>0.05$).

CONCLUSION

The peptides of the invention prevent the growth of human mammary cells in culture in an acute and concentration manner. The absence of effect on a non-mammary cell line indicates that this effect may be tissue-specific i.e. specific to human mammary cells.

The demand-led relationship between milk supply and milk removal in most, if not all, mammals predicts that the same effects as observed herein would be demonstrable in relation to the peptides of the invention obtained from milk of other species, in relation to that species. In man, administration by a suitable route of the peptides, or antibodies thereto, may be applied to improve or reduce mammary cell number. The activity of the peptides against mammary tumour cell lines suggests that the peptides may also have application in the reduction of mammary tumour cells in breast cancers.

All documents referred to in this specification are herein incorporated by reference. Various modifications and variations to the described embodiments of the inventions will be apparent to those skilled in the art without departing from the scope of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the-art are intended to be covered by the present invention.

---

The invention claimed is:

1. A method of treating human mammary epithelial cell breast cancer, the method comprising the steps of:
providing a composition comprising the peptide consisting of the amino acid sequence AVAVSQEAN (SEQ ID NO:2); and
administering a therapeutically useful amount of the composition to a subject in need of treatment through the local targeting of the mammary cells.

2. The method as claimed in claim 1 which further comprises the administration of at least one peptide selected from the group consisting of a peptide comprising the amino acid sequence RPKHPIKHQG (SEQ ID NO:1) or analogue thereof having one amino acid residue inserted, deleted or substituted, said analogue being capable of reducing mammary cell number, an analogue of the peptide comprising the amino acid sequence AVAVSQEAN (SEQ ID NO:2) having one amino acid residue inserted, deleted or substituted, said analogue being capable of reducing mammary cell number, or a peptide comprising the amino acid sequence SEGVALDPAR (SEQ ID NO:3) or analogue thereof having one amino acid residue inserted, deleted or substituted, said analogue being capable of reducing mammary cell number.

3. The method as claimed in claim 1 wherein the method further comprises the administration of a peptide comprising the amino acid sequence RPKHPIKHQG (SEQ ID NO:1) or analogue thereof having one amino acid residue inserted, deleted or substituted, said analogue being capable of reducing mammary cell number, and a peptide comprising the amino acid sequence SEGVALDPAR (SEQ ID NO:3) or analogue thereof having one amino acid residue inserted, deleted or substituted, said analogue being capable of reducing mammary cell number.

4. The method as claimed in claim 2 wherein the analogue of SEQ ID NO:2 has the amino acid sequence of SEQ ID NO:4.

* * * * *

SEQUENCE LISTING

```
<160> NUMBER OF SEQ ID NOS: 5

<210> SEQ ID NO 1
<211> LENGTH: 10
<212> TYPE: PRT
<213> ORGANISM: Bos taurus

<400> SEQUENCE: 1

Arg Pro Lys His Pro Ile Lys His Gln Gly
1               5                   10

<210> SEQ ID NO 2
<211> LENGTH: 9
<212> TYPE: PRT
<213> ORGANISM: Bos taurus

<400> SEQUENCE: 2
```

```
Ala Val Ala Val Ser Gln Glu Ala Asn
1               5

<210> SEQ ID NO 3
<211> LENGTH: 10
<212> TYPE: PRT
<213> ORGANISM: Bos taurus

<400> SEQUENCE: 3

Ser Glu Gly Val Ala Leu Asp Pro Ala Arg
1               5                   10

<210> SEQ ID NO 4
<211> LENGTH: 10
<212> TYPE: PRT
<213> ORGANISM: Artificial sequence
<220> FEATURE:
<223> OTHER INFORMATION: Cysteine residue added to C-terminal of SEQ ID
      NO: 2

<400> SEQUENCE: 4

Ala Val Ala Val Ser Gln Glu Ala Asn Cys
1               5                   10

<210> SEQ ID NO 5
<211> LENGTH: 15
<212> TYPE: PRT
<213> ORGANISM: Bos taurus

<400> SEQUENCE: 5

Arg Pro Lys His Pro Ile Lys His Gln Gly Leu Pro Glu Gln Val
1               5                   10                  15
```